United States Patent

Brahms et al.

[11] Patent Number: 5,851,513
[45] Date of Patent: Dec. 22, 1998

[54] ANTIPLAQUE ORAL COMPOSITION AND METHOD

[75] Inventors: John C. Brahms, Piscataway; Shirley A. Lucchesi, Westfield; Frederick G. Saunders, Fords; Abdul Gaffar, Princeton, all of N.J.; Stuart Shapiro, Kilchberg, Sweden

[73] Assignee: Colgate Palmolive Company, New York, N.Y.

[21] Appl. No.: 18,127

[22] Filed: Feb. 3, 1998

[51] Int. Cl.$^6$ ...................................................... A61K 7/16
[52] U.S. Cl. ................................................................ 424/49
[58] Field of Search .......................................... 424/49–58

[56] References Cited

U.S. PATENT DOCUMENTS

| | | | |
|---|---|---|---|
| 3,883,603 | 5/1975 | Inamoto et al. | 260/619 |
| 3,898,284 | 8/1975 | Bauman | 260/567.6 |
| 3,928,411 | 12/1975 | Bauman | 260/468 |
| 3,992,431 | 11/1976 | Bauman | 260/455 |
| 4,046,873 | 9/1977 | Bauman | 424/54 |
| 4,123,513 | 10/1978 | Bauman | 424/54 |
| 4,123,514 | 10/1978 | Bauman | 424/54 |
| 4,123,515 | 10/1978 | Bauman | 424/56 |
| 4,123,516 | 10/1978 | Bauman | 424/54 |
| 4,143,127 | 3/1979 | Bauman | 424/54 |
| 4,288,689 | 9/1981 | Rovatti et al. | 560/177 |
| 4,916,156 | 4/1990 | Musse et al. | 514/510 |
| 5,089,251 | 2/1992 | Mossb, II et al. | 424/47 |
| 5,221,963 | 6/1993 | Shetty | 514/635 |

OTHER PUBLICATIONS

Chem. Abstr. 83:109072 of AIGAM/ et al J. Med. Chem. 18(7):713–721 Antiviral adamantane Derivatives 2–(1–adamantyl)–4 methylphenol & Adamantyl Phenols, Adamontyl cresols (41031–50–9) (1975).

Chem. Abstr. 125:275729 of Arredondo and Biovac Med Chem. Lett 6(15):1781–1784 (Bactericidal Activity of P–1–Adamantyl Phenol) 29799–07–3, 1996.

*Primary Examiner*—Shep K. Rose
*Attorney, Agent, or Firm*—Paul Shapiro

[57] ABSTRACT

An oral composition comprising an orally acceptable vehicle and an effective antiplaque amount of at least one substantially water insoluble noncationic antibacterial agent of the formulae:

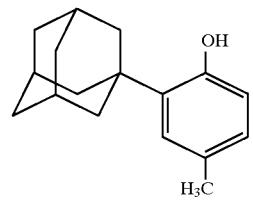

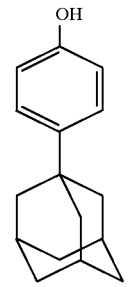

7 Claims, No Drawings

ANTIPLAQUE ORAL COMPOSITION AND METHOD

BACKGROUND OF THE INVENTION

1. Field of the Invention

This invention relates to an antibacterial antiplaque oral composition containing a substantially water insoluble, non-cationic antibacterial phenolic compound which is more fully described below.

2. The Prior Art

Dental plaque is a soft deposit which forms on teeth as opposed to calculus which is a hard calcified deposit on teeth. Unlike calculus, plaque may form on any part of the tooth surface, particularly including at the gingival margin. Hence, beside being unsightly, it is implicated in the occurrence of gingivitis.

Cationic antibacterial materials such as chlorhexidine, benzthonium chloride and cetyl pyridinium chloride have been used by the art as antibacterial antiplaque agents in oral compositions. However, such agents are generally not effective when used with anionic materials ingredients such as anionic surfactants required for the effective performance of oral compositions such as toothpaste and mouthrinses. Non-cationic antibacterial materials can be compatible with anionic components in an oral composition and noncationic halogenated hydroxydiphenyl ethers such as Triclosan have been effectively employed in oral compositions as antibacterial antiplaque agents when admixed with neutral materials such as humectants, abrasives and thickeners used in the formulation of oral compositions.

Phenol and alkyl substituted phenols are well known and widely used antimicrobials. However, it is difficult to predict the functionality of these antimicrobials as antiplaque agents when incorporated in oral composition vehicles. For example, thymol (2-isopropyl-5-methylphenol) is an active antimicrobial agent in commercial mouthrinse formulations, but its antibacterial activity is considered relatively low and possibly insufficient, its activity for example being only a small fraction of the activity of Triclosan.

SUMMARY OF THE INVENTION

In accordance with the present invention there is provided an oral antiplaque composition comprising an orally acceptable vehicle and an effective antiplaque amount of at least one substantially water insoluble noncationic adamantyl-substituted phenolic antibacterial agent having the following formulae:

and mixtures thereof.

While adamantyl substituted phenolic compounds are known (Chemical Abstracts Registration Numbers 41031-50-9 and 29799-07-3) their use as antiplaque agents delivered in an orally acceptable vehicle is not known to the prior art.

DETAILED DESCRIPTION OF THE PREFERRED EMBODIMENTS

The adamantyl substituted phenolic compound is incorporated in the oral compositions of the present invention in a non-toxic, effective antiplaque amount, typically in a range of about 0.003 to about 5%, preferably about 0.005 to about 3%, more preferably about 0.02 to about 1% by weight.

To enhance the antibacterial activity of the adamantyl-substituted phenolic antibacterial agent, an antibacterial enhancing agent may be included in the oral composition. The use of such antibacterial enhancing agents in combination with water-insoluble noncationic antibacterial compounds is known to the art, as for example, U.S. Pat. Nos. 5,188,821 and 5,192,531.

Antibacterial enhancing agents preferred for use in the practice of the present invention include a natural or synthetic anionic polymeric polycarboxylate having a molecular weight of about 1,000 to about 5,000,000, preferably about 30,000 to about 500,000. Synthetic anionic polymeric polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl either/maleic anhydride having a molecular weight (M.W.) of about 30,000 to about 1,000,000, most preferably about 30,000 to about 500,000. These copolymers are available, for example, as Gantrez®, AN 139 (M.W. 500,000), AN 119 (M.W. 250,000); and preferably S-97 Pharmaceutical Grade (M.W. 70,000), of GAF Corporation.

Other polymeric polycarboxylates useful in the practice of the present invention include the 1:1 copolymers of maleic anhydride with ethyl acrylate, hydroxyethyl methacrylate, N-vinyl-2-pyrollidone, or ethylene, the latter being available, for example, as Monsanto EMA® No: 1103, M.W. 10,000 and Grade 61, and 1:1 copolymers of acrylic acid with methyl or hydroxyethyl methacrylate, methyl or ethyl acrylate, isobutyl methacrylate, isobutyl vinyl ether or N-vinyl-2-pyrrolidone.

Additional operative useful polycarboxylate compounds include copolymers of maleic anhydride with styrene, isobutylene or ethyl vinyl either, polyacrylic, polyitaconic and polymaleic acids, and sulfonacrylic oligomers of M.W. as low as 1,000 available as Uniroyal® ND-2.

Also useful in the practice of the present invention are the so-called carboxyvinyl polymers, commercially available, for example, under the trademarks Carbopol® 934, 940 and 941 from B. F. Goodrich, these polymers consisting of a colloidally water-soluble polymer of polyacrylic acid crosslinked with from about 0.75% to about 2.0% of polyallyl sucrose or polyallyl pentaerythritol as a cross linking agent, often with M.W.'s up to 4–5 million or more.

The antibacterial enhancing agent, when employed, is incorporated in the compositions of the present invention in weight amounts of about 0.05 to about 5%, preferably about 0.1 to about 3%.

Linear molecularly dehydrated polyphosphate salts can be optionally employed herein as anticalculus agents. They are well known, being generally employed in the form of their wholly or partially neutralized water soluble alkali metal (e.g. potassium or preferably sodium) or ammonium salts, and any mixtures thereof. Representative examples include sodium tripolyphosphate, monosodium triacid,-, disodium diacid-, trisodium monoacid-, and tetrasodium-pyrophosphates, the corresponding potassium salts and the like. In the present invention, they can be employed in the oral compositions in approximate weight amounts of about 0.1 to about 3%, typically about 1 to about 2.5%, more typically about 1.5 to about 2%, especially about 2%. Particularly desirable anticalculus agents are tetraalkali metal pyrophosphates such as tetrasodium and tetrapotassium pyrophosphates, and mixtures thereof.

Fluoride ions may desirably also be included in the oral compositions of the present invention to provide an anticaries effect. Among these materials are inorganic fluoride salts, such as soluble alkali metal fluoride salts, for example, sodium fluoride, potassium fluoride, ammonium fluoride, sodium monofluorophosphate, and sodium hexafluorosilicate. Alkali metal and tin fluorides, such as sodium and stannous fluorides, sodium monofluorophosphate and mixtures thereof, are preferred.

The amount of fluorine-providing salt is generally present in the oral composition at a concentration of about 0.0005 to about 3.0% by weight. Any suitable minimum amount of such salt may be used, but it is preferable to employ sufficient fluoride salt to release about 300 to 2,000 ppm, more preferably about 800 to about 1.500 ppm, of fluoride ion.

The oral composition of the present invention may be a solution of ingredients such as a mouthrinse or it maybe a semi-solid such as a toothpaste or gel dentifrice or chewing gum or solid lozenge.

In the aspect of this invention wherein the oral composition is a gel or paste, an orally acceptable vehicle, including a water-phase with humectant which is preferably glycerine or sorbitol or an alkylene glycol such as polyethylene glycol or propylene glycol is present, wherein water is present typically in an amount of about 15–40% by weight and glycerine, sorbitol and/or the alkylene glycol (preferably propylene glycol) typically total about 20–75% by weight of the oral composition, more typically about 25–60% by weight.

When the oral composition is substantially semi-solid or pasty in character, such as a toothpaste or gel, the dentifrice vehicle may contain a dentally acceptable abrasive material such as sodium bicarbonate or water insoluble abrasive material such as sodium metaphosphate, potassium metaphosphate, tricalcium phosphate, dihydrated dicalcium phosphate, anhydrous dicalcium phosphate, calcium pyrophosphate, calcium carbonate, aluminum silicate, hydrated alumina, calcined alumina, silica, bentonite, and mixtures thereof.

The abrasive material is generally present in the paste or gel composition in weight concentrations of about 10% to about 60% by weight, preferably about 10% to about 30% in a gel and about 25% to about 60% in a paste.

Toothpastes as well as gel dentifrices typically contain a natural or synthetic thickener or gelling agent in proportions of about 0.1 to about 10% by weight, preferably about 0.5 to about 5% by weight. Suitable thickeners or gelling agents include Irish moss, iota-carrageenan, kappa-carrageenan, gum tragacanth, starch, polyvinylpyrrolidone, hydroxyethyl propyl cellulose, hydroxybutyl methyl cellulose, hydroxypropyl methyl cellulose, hydroxyethyl cellulose and sodium carboxymethyl cellulose.

In the aspect of the present invention wherein the oral composition is substantially liquid in character such as a mouthwash or rinse, the vehicle is typically a water-alcohol mixture. Generally, the weight ratio of water to alcohol is in the range of from about 3:1 to 10:1 and preferably about 4:1 to about 6:1. The alcohol is a non-toxic alcohol such as ethanol or isopropanol. A humectant such as glycerine, sorbitol or an alkylene glycol such as polyethylene glycol or preferably propylene glycol may be present in amount of about 10–30% by weight. Mouthrinses typically contain about 50–85% of water, about 0 to 20% by weight of a non-toxic alcohol and about 10–40% by weight of the humectant.

Organic surface-active agents are used in the compositions of the present invention to achieve increased prophylactic action and assist in achieving thorough and complete dispersion of the adamantyl substituted phenolic antibacterial agent throughout the oral cavity. The organic surface-active material is preferably anionic, suitable examples which include water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals and alkoyl taurines, and the like. Examples of the last mentioned amides and taurates are N-lauroyl sarcosine, and the sodium, potassium and ethanolamine salts of N-lauroyl, N-myristoyl, or N-palmitoyl sarcosine which should be substantially free from soap or similar higher fatty acid material as well as N-methyl-N-cocoyl (or oleoyl or palmitoyl) taurines.

Any suitable flavoring or sweetening material may also be employed. Examples of suitable flavoring constituents are flavoring oils, e.g. oil of spearmint, peppermint, wintergreen, sassafras, clove, sage, eucalyptus, cinnamon, lemon, and orange, and methyl salicylate. Suitable sweetening agents include sucrose, lactose, maltose, xylitol, sodium cyclamate, perillartine, aspartyl phenyl alanine methyl ester, saccharine and the like. Suitably, flavor and sweetening agents may each or together comprise from about 0.1% to 5% or more of the preparation.

Agents used to diminish teeth sensitivity such as strontium chloride, potassium nitrate and potassium citrate can also be included in the oral compositions of the present invention at concentrations of about 0.1 about 10% by weight.

Various other materials may be incorporated in the oral compositions of this invention including whitening agents such as urea peroxide, hydrogen peroxide, preservatives, such as sodium benzoate, vitamins and chlorophyll compounds. These adjuvants, when present, are incorporated in the compositions in amounts which do not substantially adversely affect the properties and characteristics desired.

The oral compositions of the present invention may be prepared by suitably mixing the ingredients. For instance, in the preparation of a mouthrinse, the adamantyl substituted phenolic antibacterial agent is dispersed in a mixture of ingredients, e.g. alcohol, humectants, surfactants, and salts such as sodium fluoride and flavor are then added and mixed. The ingredients are then mixed under vacuum for about 15–30 minutes. The resulting rinse product is then packaged. Dentifrices are prepared similarly, additional thickener and polishing agents being included in the last or penultimate step.

The compositions of this invention can be incorporated in lozenges, or in chewing gum or other products, e.g. by stirring into a warm gum base or coating the outer surface of a gum base, illustrative of which may be mentioned jelutone, rubber latex and vinylite resins desirably with conventional plasticizers or softeners, sugar or other sweeteners or carbohydrates such as glucose, sorbitol and the like.

The vehicle or carrier in a tablet or lozenge is a non-cariogenic solid water-soluble polyhydric alcohol (polyol) such as mannitol, xylitol, sorbitol, malitol, a hydrogenated starch hydrolysate hydrogenated glucose, hydrogenated disaccharides or hydrogenated polysaccharides, in an amount of about 90 to 98% by weight of the total composition. Salts such as sodium bicarbonate, sodium chloride, potassium bicarbonate or potassium chloride may totally or partially replace the polyol carrier. Tableting lubricants, in minor amounts of about 0.1 to 5% by weight, may be incorporated into the tablet or lozenge formulation to facilitate the preparation of both the tablets and lozenges. Suitable lubricants include vegetable oils such as coconut oil, magnesium stearate, aluminum stearate, talc, starch and Carbowax®.

Lozenge formulations contain about 2% gum as a barrier agent to provide a shiny surface as opposed to a tablet which has a smooth finish. Suitable non-cariogenic gums include kappa carrageenan, carboxymethyl cellulose, hydroxyethyl cellulose, Gantrez®, and the like.

The lozenge or tablet may optionally be coated with a coating material such as waxes, shellac, carboxymethyl cellulose, polyethylene/maleic anhydride copolymer or kappa-carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet and lozenge composition of this invention affords a relatively longer time period of contact of the teeth in the oral cavity with the active ingredients.

The following example further illustrates the present invention, but it is understood that the invention is not limited thereto. All amounts and proportions referred to herein and in the appended claims are by weight unless otherwise indicated.

EXAMPLE

A mouthrinse was prepared using the following ingredients:

| Ingredients | Composition A (grams) | Composition B (grams) |
| --- | --- | --- |
| Glycerin (99.7% stock) | 10.0 | 10.000 |
| Sorbitol (70% stock) | 10.0 | 10.000 |
| Ethanol | 15.0 | 15.0 |
| Propylene glycol | 15.0 | 15.0 |
| Sodium lauryl sulfate | 0.3 | 0.3 |
| Tauranol | 0.3 | 0.300 |
| Sodium fluoride | 0.243 | 0.243 |
| p-(1-adamantyl)phenol | 0.03 | — |
| 2-(1-adamantyl)-p-cresol | — | 0.03 |

The antibacterial efficacy of mouthrinse compositions A and B was evaluated in accordance with a MIC (Minimum Inhibitory Concentration) test which measures the minimum concentration in ppm of the mouthrinse at which the growth of the bacteria is completely inhibited. The smaller the MIC, the greater the antibacterial activity of the mouthrinse being tested. Water is used as a control. These MIC test is more fully described in U.S. Pat. No. 5,275,805 at column 11, lines 54–68, which description is herewith incorporated herein.

The results of the MIC tests are recorded in the table below:

TABLE

| | A. viscosus (MIC in ppm) |
| --- | --- |
| Mouthrinse A | 15.6 |
| Mouthrinse B | 15.6 |
| Control (water) | <125 |

The results recorded in the Table demonstrate that mouthrinses containing an adamantyl substituted phenol are effective as antiplaque oral compositions.

What is claimed is:

1. An oral composition comprising an orally acceptable mouthrinse, toothpaste, gel dentifrice, chewing gum or lozenge vehicle and an effective antiplaque amount of at least about 0.003% by weight of at least one substantially water insoluble noncationic adamantyl phenol antibacterial agent of the formulae:

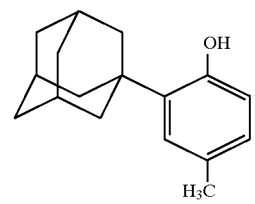

-continued

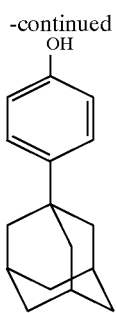

and mixtures thereof.

2. The composition of claim 1 wherein the antibacterial agent is present in the oral composition in a amount in the range of about 0.003 to about 5.0% by weight.

3. The composition of claim 1 wherein an anionic polycarboxylate antibacterial enhancing agent is incorporated in the composition.

4. The composition of claim 3 wherein the anionic polycarboxylate is a maleic anhydride copolymer.

5. A composition according to claim 1 wherein the composition is in the form of a mouthrinse.

6. A composition according to claim 1 in the form of a dentifrice containing a dentally acceptable polishing agent and a vehicle comprising water and humectant.

7. A method of promoting oral hygiene comprising applying to dental surface an effective amount of a composition as defined in claim 1.

* * * * *

UNITED STATES PATENT AND TRADEMARK OFFICE
CERTIFICATE OF CORRECTION

PATENT NO. : 5,851,513

DATED : December 22, 1998

INVENTOR(S) : Brahms, et al.

It is certified that error appears in the above-identified patent and that said Letters Patent is hereby corrected as shown below:

```
On the title page:
   Item [75], "Stuart Shapiro
           Kilchberg, Sweden"   should read --Stuart Shapiro
         Kilchberg, Switzerland--
```

Signed and Sealed this

Twenty-seventh Day of April, 1999

Attest:

Q. TODD DICKINSON

*Attesting Officer*                *Acting Commissioner of Patents and Trademarks*